United States Patent [19]
Mammone et al.

[11] Patent Number: 6,149,925
[45] Date of Patent: Nov. 21, 2000

[54] TOPICAL COMPOSITIONS FOR ENHANCING GLUTATHIONE PRODUCTION

[75] Inventors: Thomas Mammone, Farmingdale; David C. Gan, Dix Hills, both of N.Y.

[73] Assignee: Color access, Inc., Melville, N.Y.

[21] Appl. No.: 09/186,525

[22] Filed: Nov. 5, 1998

[51] Int. Cl.⁷ .............................. A61K 7/00; A61K 38/00; A61K 31/195; A61K 31/095
[52] U.S. Cl. .............................. 424/401; 514/18; 514/562; 514/563; 514/706; 514/844
[58] Field of Search ................................ 424/401; 514/18, 514/562, 563, 706, 844

[56] References Cited

U.S. PATENT DOCUMENTS

| | | | |
|---|---|---|---|
| 4,710,489 | 12/1987 | Meister | 514/18 |
| 5,248,697 | 9/1993 | Wilmore | 514/563 |
| 5,296,500 | 3/1994 | Hillebrand | 514/562 |
| 5,709,868 | 1/1998 | Perricone | 424/401 |

FOREIGN PATENT DOCUMENTS

| | | |
|---|---|---|
| 6279227 | 10/1994 | Japan . |
| 2180153 | 3/1987 | United Kingdom . |

OTHER PUBLICATIONS

Correlation Between Endogenous Glutathione Content and Sensitivity of Cultured Human Skin Cells To Radiation At Defined Wavelengths in the Solar Ultraviolet Range, R. M. Tyrrell and M. Pidoux, Photochemistry and Photobiology, vol. 47, No. 3, pp. 405–412, 1988.

Alton Meister, Glutathione Metabolism and its Selective Modification, The Journal of Biological Chemistry,vol. 263, No. 33, Issue of Nov. 25, pp. 17205–17208, 1988.

Alton Meister, Selective Modification of Glutathione Metabolism, Science, vol. 220, Apr. 1983, pp. 471–477.

*Primary Examiner*—Shelley A. Dodson
*Assistant Examiner*—Marina Lamm
*Attorney, Agent, or Firm*—Kenyon & Kenyon

[57] ABSTRACT

The invention provides cosmetic or pharmaceutical compositions for topical application to the skin comprising glutathione-enhancing effective amounts of a glycine compound, a glutamine compound, and a sulfhydryl-containing organic acid, in a cosmetically or pharmaceutically acceptable carrier. The compositions are useful in increasing glutathione synthesis in skin cells, and in treating skin conditions associated with glutathione depletion in skin cells.

14 Claims, 5 Drawing Sheets

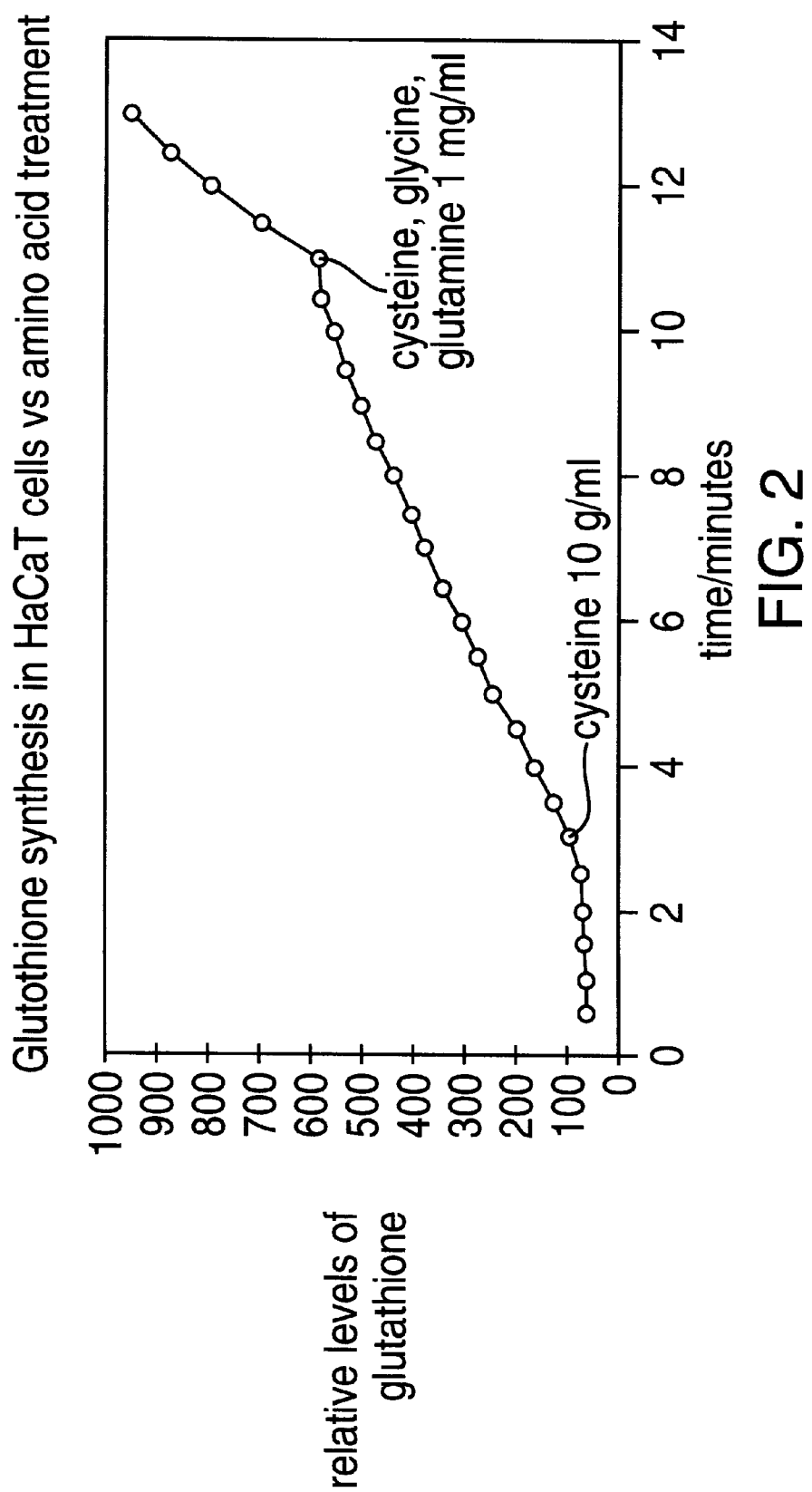

ns for ENHANCING GLUTATHIONE PRODUCTION

FIELD OF THE INVENTION

The present invention relates to skin care compositions. More specifically, the invention relates to compositions useful in reducing or eliminating free radical damage to the skin.

BACKGROUND OF THE INVENTION

Thousands of biochemical processes are ongoing in the living body at any given time. Many of these endogenous aerobic processes naturally give rise, as by-products, to very highly reactive molecules. A large number of these reactive molecules are known generally as free radicals, which are defined as an atom or group of atoms with an unpaired electron. However, other non-free radical reactive species are also generated by these processes. The processes that produce the reactive entities may be enzymatic, such as those involved in phagocytosis, respiration, the cytochrome P-450 system and prostaglandin synthesis; or they may be non-enzymatic, such as the reaction of oxygen with organic compounds, or reactions initiated by ionizing radiation. These reactive molecules, if uncontrolled, may rapidly, and randomly, react with molecules in their vicinity, giving rise to toxic products that can interfere with the body's normal physiological processes. Considerable evidence exists that unchecked free radical reactions have some, if not major, involvement, in a number of disease states, for example, emphysema, inflammation, cancer, atherosclerosis and cataracts. Free radical reactions are also widely considered to have a major contributory effect on the natural aging process.

Among the most reactive of all regularly produced reactive species, and biologically among the most important, are those containing oxygen. These include, for example, partially reduced oxygen free radicals such as superoxide anion radicals, hydrogen peroxide and hydroxyl ions, as well as singlet oxygen. The latter, while not strictly speaking a free radical, as it technically possesses paired electrons, can be conveniently grouped with the oxygen-centered radicals, as its distorted electron configuration confers a high level of reactivity, and it is therefore potentially similarly toxic. These reactive oxygen species have been implicated in a number of reactions that can cause serious damage to cellular components: for example, oxidizing radicals can attack the bases and sugar molecules of DNA, altering the molecular structure and thereby interfering with biological functions. They may also interact with unsaturated fatty acids in cell membranes, causing lipid peroxidation, which results not only in alteration of the protein:lipid interaction of the membrane, but in the production of breakdown products which can exert a host of undesired effects, such as inhibition of DNA synthesis, adenyl cyclase and glucose-6-phosphate, increase in capillary permeability and inhibition of platelet aggregation.

Because molecular oxygen is virtually everywhere and it freely accepts electrons, these oxygen-centered radicals are probably the most common mediators of cellular free radical reactions. They are of course routinely produced as a result of aerobic metabolism. However, a very significant amount is generated as a result of photochemical reactions. Any organic or inorganic compound will absorb some UV radiation, and the absorbed energy will promote chemical reactions. There are a variety of recognized mechanisms by which light can cause the generation of oxygen-centered radicals; regardless of the mechanism, however, it is clear that the interaction of sunlight with organic or inorganic substrates on exposed skin can result in one or more reactive oxygen species being produced on the skin. It has been recognized in recent years that the presence of oxygen radicals on the skin is probably responsible for a number of the undesirable effects of prolonged exposure to the sun. For example, the aging phenomenon generally observed throughout the body is frequently observed prematurely on the skin as a result of photoaging, which accelerates the process of deterioration of elastin and collagen, among other effects. There is also an increased risk of skin cancer of all types.

The body has a number of defenses that can, under normal circumstances, to a large extent keep the potential damage resulting from these reactions in check. One of the most important of the naturally occurring defense mechanisms is the tripeptide glutathione comprising glutamic acid, cysteine, and glycine residues, and which is found in most cell types in the body. This compound has very significant free radical scavenging properties, and is believed to play a significant role in protecting cells against the cytotoxic effects of ionizing radiation, heat, certain chemicals, and significantly, solar UV radiation (Tyrell et al., Photochem. Photobiol. 47: 405–412, 1988) The mechanism by which glutathione protects cells against oxidative attack is complex, and involves a number of additional biochemical players; however, it is well established that a naturally occurring pathway involving glutathione and several glutathione-associated enzymes is capable of reducing a wide variety of organic hydroperoxides, thereby preventing substantial cellular oxidative damage. Indeed, it has also been shown that depletion or elimination of cellular glutathione can result in cellular sensitization to radiation, oxidative stress, decreased synthesis of leukotrienes and prostaglandins, inhibition of thermotolerance, decrease lymphocyte response to mitogens, and increased response to teratogens (Dolphin et al., eds., *Glutathione: Chemical, Biochemical and Medical Aspects, Part A Series, Coenzymes and Cofactors*. John Wiley and Sons, NY, 1989; Meister, J. Biol. Chem. 263: 205–217, 1988; Meister, Science 200: 471–477, 1985).

Clearly, a substantial intracellular supply of glutathione is critical to protect cells from the daily oxidative stress to which they are subjected, and given the broad array of exogenous stimuli which tax this system, it is expected that naturally occurring supply will be routinely depleted. While true in all areas of the body, this is particularly important in the skin, which is so greatly exposed to the damaging effects of radiation, particularly UV radiation. It is, therefore, highly desirable to determine a means of enhancing the generation of glutathione in cells, so as to maintain or replenish cellular levels which can readily respond to daily environmental insults. While a logical approach would seem to be to provide cells with an exogenous source of glutathione, the compound is not transported into the cells and therefore does not result in an intracellular accumulation of glutathione. Thus, there continues to be a need for finding alternate sources of glutathione enhancement. The present invention fill such a need.

SUMMARY OF THE INVENTION

The present invention relates to topical compositions for application to the skin which comprise glutathione-enhancing effective amounts of glutamine, glycine and a cosmetically acceptable sulfur-containing organic acid. Preferably, the sulfur-containing acid is an amino acid, such as cysteine, N-acetyl cysteine, cystine, or a non-amino acid, such as lipoic acid. The invention also relates to a method of increasing glutathione levels in skin cells, as well as a method for preventing or alleviating free radical damage to skin cells, which comprises applying to the skin a composition containing the designated amino acid combination.

BRIEF DESCRIPTION OF THE DRAWINGS

FIG. 2 illustrates graphically a comparison of the increase in glutathione production using one amino acid (L-cysteine) versus a combination of amino acids (L-glycine, L-glutamine, and L-cysteine).

DETAILED DESCRIPTION OF THE INVENTION

Figure 1A:
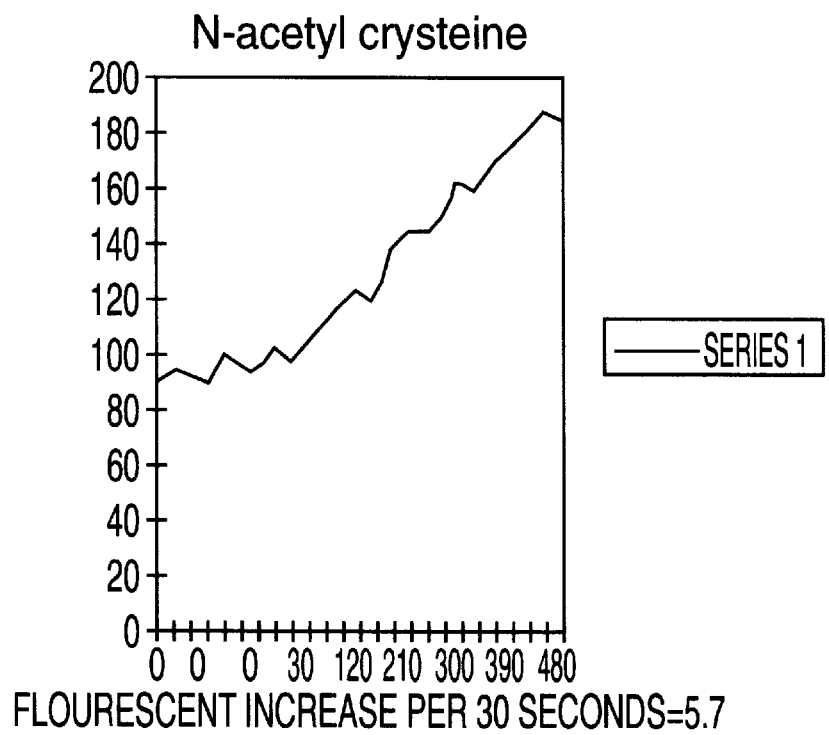
FIG. 1 illustrates graphically the effects of various amino acids, alone or in combination, on glutathione production in cultured cells, using a plot of fluorescence levels over time as an indicator of glutathione levels. The identity of the amino acids are as follows: (A) N-acetyl cysteine; (B) L-glutamine; (C) L-glutamine and N-acetyl cysteine; (D) N-acetyl cysteine; (E) N-acetyl glutamine; (F) N-acetyl glutamine and N-acetyl cysteine.

It has been now discovered that a combination of three acidic components have unexpectedly potent effect in enhancing glutathione production in skin cells. This observation has resulted in the development of novel compositions for topical application to the skin, containing at least one of each of glutamine, glycine, and a sulfhydryl-containing organic acid, or a cosmetically acceptable derivative of any of these.

Each of the basic components of the composition is a known compound, and each has been known for other biological activities. For example, glutamine and glycine have been shown to play roles in neurotransmission in the central nervous system. Glutamine has also been used in systemically administered compositions to treat conditions associated with low glutathione levels, such as cancer or sepsis, or tissue damage due to radiation (U.S. Pat. No. 5,248,697). Sulfhydryl-containing organic acids, e.g., N-acetyl cysteine or lipoic acid, have been previously identified as having antioxidant activity (U.S. Pat. Nos. 5,296, 500 and 5,709,868). In addition, N-acetyl cysteine has been stated as having an effect on restoration of useful concentrations of endogenous glutathione (GB 2180153). However, to Applicants' knowledge, although each of the components has been previously used individually in cosmetic compositions for various purposes(e.g., JP 6279227), the three components have not previously been used in combination in topical compositions to enhance glutathione synthesis in skin cells. Indeed, the combination of these components results in a synergistic enhancement of glutathione in skin cells when applied topically in effective amounts. It is noteworthy in this regard that glycine alone, except at very high levels, does not appear to have any significant effect on glutathione, nor does its combination with glutamine. In addition, the combination of glycine with N-acetyl cysteine, which itself does enhance glutathione, does not show any substantial increase over the effect of N-acetyl cysteine alone. However, the combination of glycine, glutamine and N-acetyl cysteine provides a very substantial increase in glutathione synthesis, beyond what is observed in any other two component combination tested. Similar results are observed with the combination of glycine, glutamine and L-cysteine. Preferably, the enhancement observed with the combination of components is at least about twice the baseline level, preferably at least three times the baseline level of glutathione, as measured by fluorescence increase in treated trypsinized cells when monochlorobimane is added.

The glycine component of the formulation can be glycine per se, but may also be a cosmetically acceptable glycine derivative. Similarly, although glutamine per se is preferred, it is also possible to employ glutamine derivatives. The sulfhydryl-containing organic acid can be an amino acid, such as cysteine or cystine, or a non-amino acid such as lipoic acid; in addition, this component can be a cosmetically acceptable derivative of any of these, for example, esters, amines, salts and the like. The concentration of each compound used may vary, but will generally be in the range of from about 0.01–20%, preferably from about 0.05–10%, and more preferably from about 0.5–3% of any each component. It is preferred that the components are used in approximately equal amounts.

For topical application, the antioxidant mixture can be combined with a cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton Pa., 1990. The carrier may be in any form appropriate to the mode of delivery, for example, solutions, colloidal dispersions, emulsions (oil-in-water or water-in-oil), suspensions, creams, lotions, gels, foams, mousses, sprays and the like.

The formulation, in addition to the carrier and the antioxidant mixture, also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like. The composition can be a therapeutic product, the required components being the sole actives, or in combination with other actives. Examples of such actives include, but are not limited to, sunscreens and sunblocks, antiaging actives, antioxidants, and antiinflammatories. However, the combination can also be used as part of a makeup product, for example, a lipstick, foundation, concealer, bronzer, blush, eyeshadow and the like.

The compositions of the invention enhance the synthesis of glutathione in skin cells, and therefore, can be used to treat any skin condition in which glutathione depletion is potentially a factor. A preferred use of the compositions of the invention is in the treatment and/or prevention of the symptoms of chronoaging or photoaging, the treatment and/or prevention of immediate damage resulting from excessive exposure to UV radiation, sun as prolonged sun exposure and therapeutic radiation, and treatment and/or prevention of cellular damage due to chemotherapy. For these purposes, the compositions of the invention can be applied on an as-needed basis, for example, applied to the skin before anticipated prolonged sun exposure, or during or after such exposure. However, a preferred method of obtaining the benefits of the composition is via chronic topical application of a safe and effective amount of a composition containing the mixture, to prevent development of skin damage which may result from even routine exposure to UV light or other environmental insults which may result in the generation of reactive oxygen species, or to prevent worsening of or to reverse existing damage. It is suggested as an example that topical application of the composition, in an amount of from about 0.1 $\mu g/cm^2$ to 2 $mg/cm^2$ of exposed skin, be performed from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months to about ten years, more preferably still from about one year to about five years, thereby resulting in the treatment or prevention of the external signs of photoaging. It will be recognized by those skilled in the art that the treatment regimen employed can be varied depending upon the user's level of exposure to noxious stimuli; a chronically sun-exposed individual may benefit from more frequent applications than will be necessary for an individual who avoids the sun.

The invention is further illustrated by the following non-limiting examples.

EXAMPLES

Example I

A composition according to the invention is prepared as follows:

| Material | Weight % |
| --- | --- |
| Phase I | |
| Cetyl alcohol | 1.65 |
| glyceryl monostearate | 1.65 |
| glyceryl stearate/PEG 100 stearate | 6.60 |
| cetearyl alcohol | 1.00 |
| caprylic/capric/stearic triglyceride | 0.50 |
| dimethicone | 0.40 |
| coco-caprylate/caprate | 3.60 |
| polysorbate 40 | 0.66 |
| sorbitan palmitate | 0.44 |
| Dioctyl adipate/octyl stearate/ octyl palmitate | 3.30 |
| Phase II | |
| deionized water | 51.50 |
| 1,3 butylene glycol | 6.00 |

| Material | Weight % |
| --- | --- |
| trisodium EDTA | 0.10 |
| N-acetyl cysteine | 0.50 |
| Phase III | |
| deionized water | 20.00 |
| glycine | 1.00 |
| L-glutamine | 1.00 |

Example II

Figure 1B:
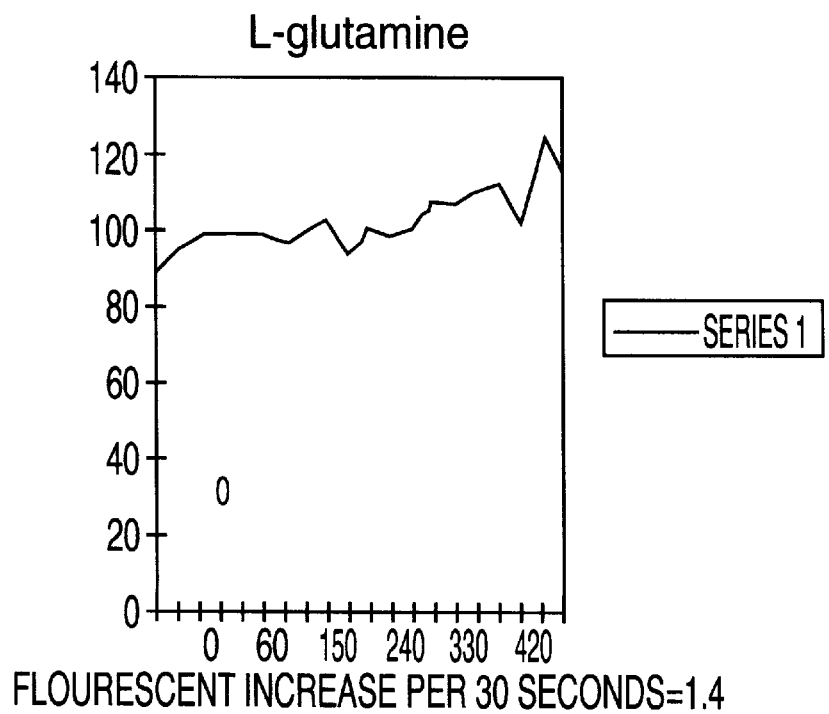
Figure 1C:
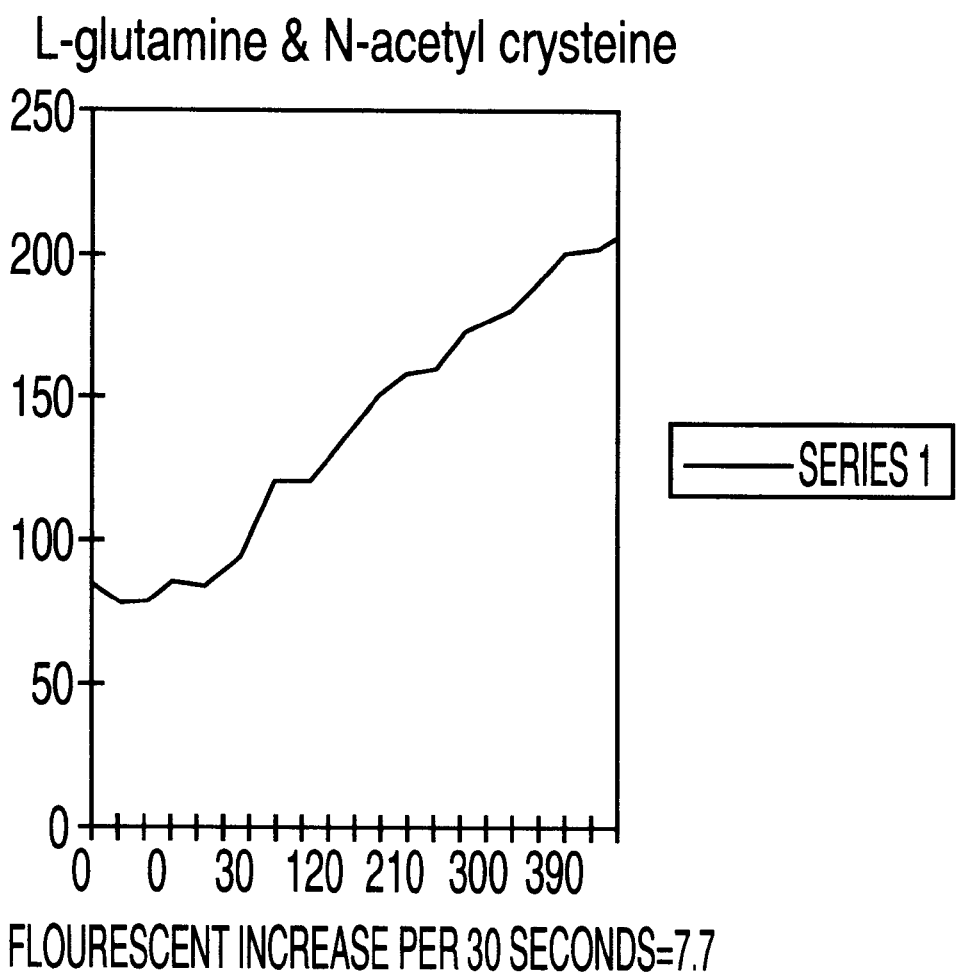
Figure 1D:
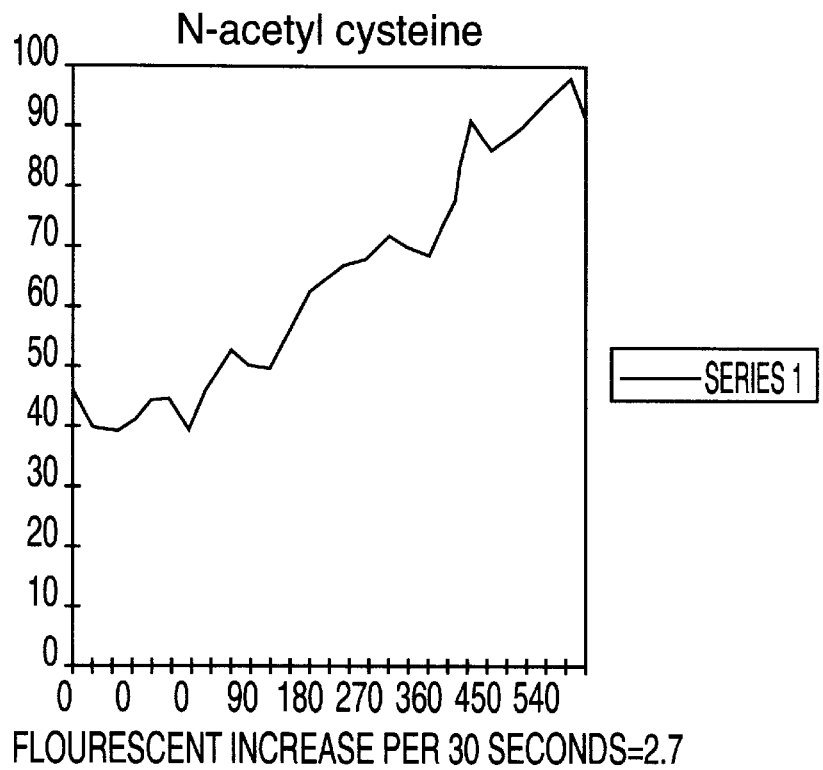
Figure 1E:
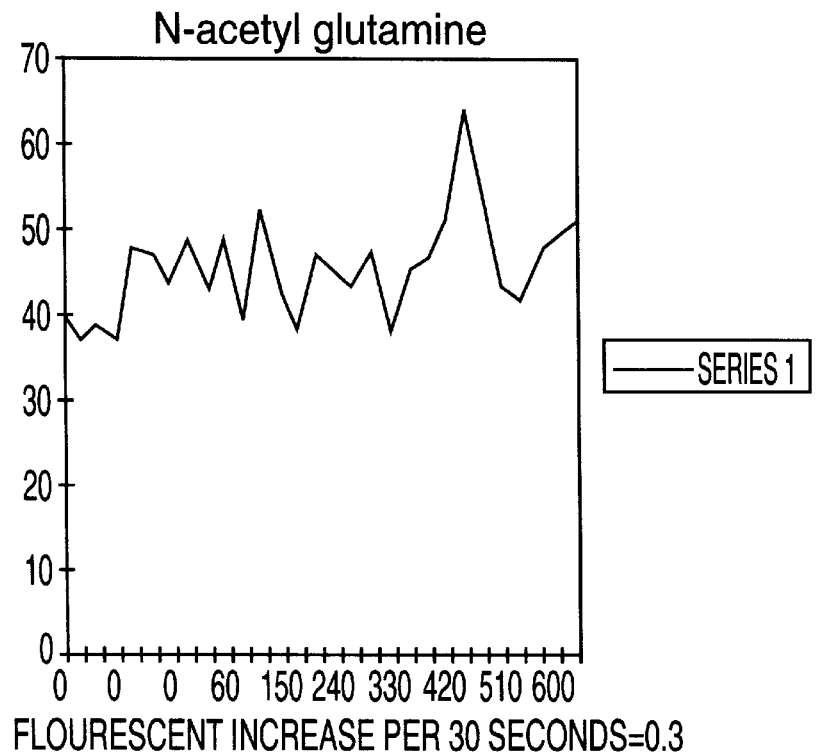
Figure 1F:
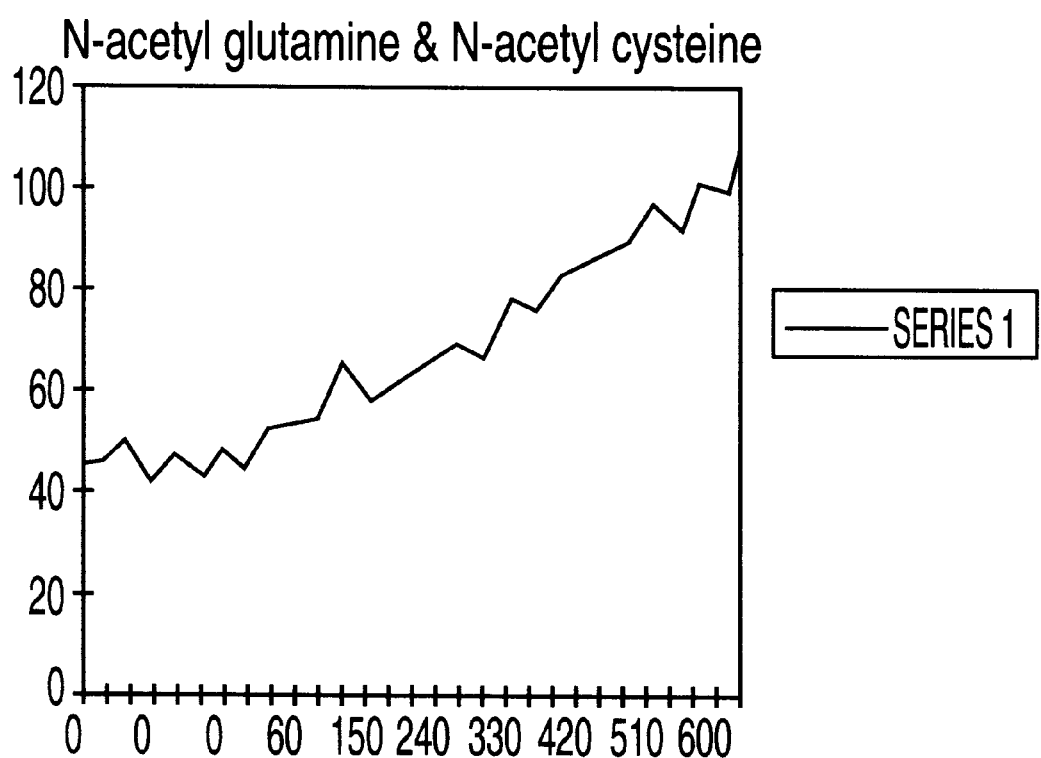

This example illustrates the efficacy of compositions of the present invention:

Each of the components of the composition is tested separately, and then in combination with other components, as follows. Confluent Hacat cells are trypsinized and resuspended in PBS. Monochlorobimane is added to the cells and the fluorescent baseline is determined(time=0). A 1:10 volume of 5 mg/ml of N-acetyl cysteine is added to the cell sample to be used as a control. In a pilot study with a different group of Hacat cells, glycine is added at 10 mg/ml, then increased to 20 mg/ml. Fluorescence is measured every 30 seconds. A graph of fluorescence versus time is plotted and the increase in fluorescence over time is used as a measure of glutathione synthesis. The experimental procedure is repeated with glycine alone, glutamine alone, glycine combined with N-acetyl cysteine, glycine combined with L-glutamine, and all three components combined; each component is used in an amount of 1%, except for N-acetyl cysteine, which is used at 0.5%. The results are shown in FIGS. 1(A)–1(F). The data can be summarized as follows: glycine alone at low dosage yields a fluorescent increase per 30 seconds of 1.0 fluorescent unit, and at high dosage, 3.2. The fluorescent increase per 30 seconds for N-acetyl cysteine alone is 2.7. In a second test of glycine alone, the increase is 0.0. The combination of glycine and N-acetyl cysteine alone yields an increase of 4.7. Glycine and glutamine yield an increase of 0.1. Glutamine alone (data not shown) does not yield any increase in glutathione. The combination of all three components produces a fluorescent increase of 5.4. These results indicate an unexpected increase in glutathione production resulting from the combination of all three components added to the cells.

Similar experiments are conducted with the L-cysteine in place of N-acetyl cysteine. A 1:10 volume of 10 mg/ml of L-cysteine is added to the cell samples, and fluorescence measured every 30 second. A graph of fluorescence versus time is plotted and the increase in fluorescence over time is used as a measure of glutathione synthesis. L-cysteine (10 mg/ml), glycine (10 mg/ml) and L-glutamine (10 mg/ml) are added following the first treatment. A graphic depiction of the results is shown in FIG. 2. The results are expressed in fluorescent units of glutathione per minute. A baseline increase of 3.6 is observed, followed by and increase of 61.325 with the addition of L-cysteine, and an increase of 181.2 with a combination of L-glycine, L-glutamine and L-cysteine, again demonstrating the synergistic interaction of the three components.

What we claim is:

1. A method of enhancing glutathione levels in skin cells which comprises applying to the skin a cosmetic or pharmaceutical composition comprising effective amounts of a glycine compound, a glutamine compound, and a sulfhydryl-containing organic acid, in a cosmetically or pharmaceutically acceptable carrier.

2. The method of claim 1 in which the organic acid is selected from the group consisting of cysteine, N-acetyl cysteine, and lipoic acid.

3. The method of claim 1 in which the effective amount is from about 0.01–20%, by weight of the total composition, of each component.

4. The method of claim 1 in which the effective amount is from about 0.05–10% by weight of the total composition, of each component.

5. The method of claim 1 in which the effective amount is from about 0.5–3% by weight of the total composition, of each component.

6. The method of claim 1 in which the composition comprises glycine, glutamine and lipoic acid.

7. The method of claim 1 in which the composition comprises glycine, glutamine and N-acetyl cysteine.

8. The method of claim 6 in which the effective amounts of each component is from about 0.5–3% by weight of the composition, each component being present in approximately equal amounts.

9. The method of claim 7 in which the effective amounts of each component is from about 0.5–3% by weight of the composition, each component being present in approximately equal amounts.

10. A method for treating or preventing a skin condition associated with glutathione depletion which comprises applying to skin a cosmetic or pharmaceutical composition comprising effective amounts of a glycine compound, a glutamine compound, and a sulfhydryl-containing organic acid, in a cosmetically or pharmaceutically acceptable carrier.

11. The method of claim 10 in which the organic acid is selected from the group consisting of cysteine, N-acetyl cysteine, and lipoic acid.

12. The method of claim 10 in which the effective amount is from about 0.01–20%, by weight of the total composition, of each component.

13. The method of claim 10 in which the effective amount is from about 0.05–10% by weight of the total composition, of each component.

14. The method of claim 10 in which the effective amount is from about 0.5–3% by weight of the total composition, of each component.

* * * * *